United States Patent
Haller et al.

(10) Patent No.: US 7,627,383 B2
(45) Date of Patent: Dec. 1, 2009

(54) IMPLANTABLE STIMULATOR

(75) Inventors: Matthew I. Haller, Valley Village, CA (US); Jay Daulton, Gilroy, CA (US); Todd K. Whitehurst, Santa Clarita, CA (US); Rafael Carbunaru, Studio City, CA (US)

(73) Assignee: Boston Scientific Neuromodulation Corporation, Valenica, CA (US)

( * ) Notice: Subject to any disclaimer, the term of this patent is extended or adjusted under 35 U.S.C. 154(b) by 152 days.

(21) Appl. No.: 11/081,417

(22) Filed: Mar. 15, 2005

(65) Prior Publication Data

US 2006/0212087 A1 Sep. 21, 2006

(51) Int. Cl.
*A61N 1/36* (2006.01)

(52) U.S. Cl. .............................. 607/116; 607/39; 607/41
(58) Field of Classification Search ................. 607/1–3, 607/48–52, 59–61, 116; 600/554, 302, 377, 600/114; 606/129
See application file for complete search history.

(56) References Cited

U.S. PATENT DOCUMENTS

| | | |
|---|---|---|
| 3,850,161 A | 11/1974 | Liss |
| 3,881,495 A | 5/1975 | Pannozzo et al. |
| 4,232,679 A | 11/1980 | Schulman |
| 4,408,608 A | 10/1983 | Daly |
| 4,481,950 A | 11/1984 | Duggan |
| 4,562,751 A | 1/1986 | Nason et al. |
| 4,590,946 A | 5/1986 | Loeb |
| 4,608,985 A | 9/1986 | Crish |
| 4,628,942 A | 12/1986 | Sweeney et al. |
| 4,649,936 A | 3/1987 | Ungar |
| 4,678,408 A | 7/1987 | Nason et al. |
| 4,685,903 A | 8/1987 | Cable et al. |
| 4,702,254 A | 10/1987 | Zabara |
| 4,793,353 A | 12/1988 | Borkan |
| 5,080,653 A | 1/1992 | Voss et al. |
| 5,095,904 A | 3/1992 | Seligman |
| 5,097,122 A | 3/1992 | Colman et al. |
| 5,188,104 A | 2/1993 | Wernicke et al. |
| 5,193,539 A | 3/1993 | Schulman et al. |
| 5,193,540 A | 3/1993 | Schulman et al. |
| 5,199,430 A | 4/1993 | Fang |
| 5,215,086 A | 6/1993 | Terry, Jr. et al. |
| 5,234,692 A | 8/1993 | Magruder et al. |
| 5,234,693 A | 8/1993 | Magruder et al. |
| 5,299,569 A | 4/1994 | Wernicke et al. |
| 5,305,445 A | 4/1994 | Nishikawa |

(Continued)

FOREIGN PATENT DOCUMENTS

WO WO 2007/059343 5/2007

*Primary Examiner*—Mark W Bockelman
(74) *Attorney, Agent, or Firm*—Vista IP Law Group LLP

(57) ABSTRACT

Exemplary implantable stimulators for stimulating a stimulation site within a patient include an electronic module configured to generate stimulation and a housing configured to house the electronic module. The housing has a shape allowing the a stimulator and a surgical device to be accommodated together within an insertion tool used to insert the stimulator into the patient. Exemplary methods of stimulating a stimulation site within a patient include generating stimulation with an electronic module and housing the electronic module in a housing. The housing has a shape allowing the housing and a surgical device to be accommodated together within an insertion tool used to insert the housing into the patient.

19 Claims, 10 Drawing Sheets

U.S. PATENT DOCUMENTS

| | | | |
|---|---|---|---|
| 5,305,745 A | 4/1994 | Zacouto | |
| 5,312,439 A | 5/1994 | Loeb | |
| 5,314,451 A | 5/1994 | Mulier | |
| 5,314,458 A * | 5/1994 | Najafi et al. | 607/116 |
| 5,330,515 A | 7/1994 | Rutecki et al. | |
| 5,358,514 A * | 10/1994 | Schulman et al. | 607/61 |
| 5,405,363 A | 4/1995 | Kroll et al. | |
| 5,501,703 A | 3/1996 | Holsheimer et al. | |
| 5,531,787 A | 7/1996 | Lesinski et al. | |
| 5,700,282 A | 12/1997 | Zabara | |
| 5,716,318 A | 2/1998 | Manning | |
| 5,728,396 A | 3/1998 | Peery et al. | |
| 5,752,979 A | 5/1998 | Benabid | |
| 5,755,750 A | 5/1998 | Petruska et al. | |
| 5,782,891 A | 7/1998 | Hassler et al. | |
| 5,895,416 A | 4/1999 | Barreras, Sr. et al. | |
| 5,938,584 A | 8/1999 | Ardito et al. | |
| 5,938,688 A | 8/1999 | Schiff | |
| 5,995,868 A | 11/1999 | Dorfmeister et al. | |
| 6,016,449 A | 1/2000 | Fischell et al. | |
| 6,051,017 A | 4/2000 | Loeb et al. | |
| 6,061,596 A | 5/2000 | Richmond et al. | |
| 6,104,956 A | 8/2000 | Naritoku et al. | |
| 6,112,116 A | 8/2000 | Fischell et al. | |
| 6,154,678 A | 11/2000 | Lauro | |
| 6,164,284 A | 12/2000 | Schulman | |
| 6,175,764 B1 | 1/2001 | Loeb et al. | |
| 6,178,349 B1 | 1/2001 | Kieval | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,205,359 B1 | 3/2001 | Boveja | |
| 6,208,894 B1 | 3/2001 | Schulman et al. | |
| 6,214,032 B1 | 4/2001 | Loeb et al. | |
| 6,216,045 B1 | 4/2001 | Black et al. | |
| 6,219,580 B1 | 4/2001 | Faltys et al. | |
| 6,266,564 B1 | 7/2001 | Hill et al. | |
| 6,272,382 B1 | 8/2001 | Faltys et al. | |
| 6,275,737 B1 | 8/2001 | Mann | |
| 6,308,101 B1 | 10/2001 | Faltys et al. | |
| 6,341,236 B1 | 1/2002 | Osorio et al. | |
| 6,368,315 B1 | 4/2002 | Gillis et al. | |
| 6,381,496 B1 | 4/2002 | Meadows et al. | |
| 6,424,234 B1 | 7/2002 | Stevenson | |
| 6,473,652 B1 | 10/2002 | Sarwal et al. | |
| 6,487,446 B1 | 11/2002 | Hill et al. | |
| 6,516,227 B1 | 2/2003 | Meadows et al. | |
| 6,526,318 B1 | 2/2003 | Ansarinia | |
| 6,539,263 B1 | 3/2003 | Schiff et al. | |
| 6,553,263 B1 | 4/2003 | Meadows et al. | |
| 6,560,490 B2 | 5/2003 | Grill | |
| 6,582,441 B1 | 6/2003 | He et al. | |
| 6,597,954 B1 | 7/2003 | Pless et al. | |
| 6,600,954 B2 | 7/2003 | Cohen et al. | |
| 6,620,151 B2 | 9/2003 | Blischak | |
| 6,622,048 B1 | 9/2003 | Mann et al. | |
| 6,650,943 B1 * | 11/2003 | Whitehurst et al. | 607/39 |
| 6,662,035 B2 | 12/2003 | Sochor | |
| 6,665,562 B2 | 12/2003 | Gluckman et al. | |
| 6,666,845 B2 | 12/2003 | Hooper et al. | |
| 6,712,753 B2 | 3/2004 | Manne | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,782,292 B2 | 8/2004 | Whitehurst | |
| 6,826,428 B1 | 11/2004 | Chen et al. | |
| 6,907,295 B2 | 6/2005 | Gross et al. | |
| 6,928,320 B2 | 8/2005 | King | |
| 7,072,720 B2 | 7/2006 | Puskas | |
| 7,203,548 B2 | 4/2007 | Whitehurst et al. | |
| 7,292,890 B2 | 11/2007 | Whitehurst et al. | |
| 2001/0003799 A1 | 6/2001 | Boveja | |
| 2002/0016615 A1 | 2/2002 | Dev et al. | |
| 2002/0022873 A1 | 2/2002 | Erickson et al. | |
| 2003/0004546 A1 | 1/2003 | Casey | |
| 2003/0083698 A1 | 5/2003 | Whitehurst et al. | |
| 2003/0203890 A1 | 10/2003 | Steiner et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0034394 A1 | 2/2004 | Woods et al. | |
| 2004/0172089 A1 | 9/2004 | Whitehurst et al. | |
| 2004/0243182 A1 | 12/2004 | Cohen et al. | |
| 2005/0004619 A1 | 1/2005 | Wahlstrand et al. | |
| 2005/0101878 A1 | 5/2005 | Daly et al. | |
| 2005/0113894 A1* | 5/2005 | Zilberman et al. | 607/116 |
| 2005/0245971 A1 | 11/2005 | Brockway et al. | |
| 2006/0136004 A1* | 6/2006 | Cowan et al. | 607/33 |
| 2006/0184204 A1 | 8/2006 | He | |
| 2006/0195143 A1 | 8/2006 | McClure et al. | |
| 2007/0021800 A1 | 1/2007 | Whitehurst et al. | |

* cited by examiner

IMPLANTABLE STIMULATOR

BACKGROUND

Radio-frequency (RF) powered implantable stimulators and battery powered implantable stimulators are described in the art. See, for instance, U.S. Pat. No. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both titled "System of Implantable Device for Monitoring and/or Affecting Body Parameters"). Each of these patents is incorporated herein by reference in its respective entirety.

Implantable stimulators may be used to provide therapy such as nerve and/or muscle stimulation, for various purposes. For example, urinary urge incontinence may be treated by stimulating the nerve fibers proximal to the pudendal nerves of the pelvic floor; erectile or other sexual dysfunctions may be treated by providing stimulation of the cavernous nerve; and other disorders, e.g., neurological disorders caused by injury or stroke, may be treated by providing stimulation of other appropriate nerves.

Additionally, implantable stimulators configured to prevent and/or treat various disorders associated with prolonged inactivity, confinement or immobilization of one or more muscles are taught, e.g., in U.S. Pat. No. 6,061,596 ("Method for Conditioning Pelvis Musculature Using an Implanted Microstimulator"); U.S. Pat. No. 6,051,017 ("Implantable Microstimulator and Systems Employing the Same"); U.S. Pat. No. 6,175,764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). Each of these patents is incorporated herein by reference in its respective entirety.

Many implantable stimulators require very precise placement within the body of a patient in order to satisfy the intended function, such as stimulators having electrodes that are used to stimulate specific nerves. If an electrode is not initially positioned close enough to stimulate the targeted nerve, additional surgery may be required to reposition the stimulator and/or electrode. Consequently, specialized surgical tools have been developed to facilitate the precise implantation of implantable stimulators. See, for instance, U.S. Pat. No. 6,582,441 ("Surgical Insertion Tool"), which patent is incorporated herein by reference in its entirety. Surgeons often prefer to use a laparoscope during the implantation procedure so that they can visually ensure that the stimulator is properly placed in the correct location within the patient.

SUMMARY

Exemplary implantable stimulators for stimulating a stimulation site within a patient include an electronic module configured to generate stimulation and a housing configured to house the electronic module. The housing has a shape allowing a stimulator and a surgical device to be accommodated together within an insertion tool used to insert the stimulator into the patient.

Exemplary methods of stimulating a stimulation site within a patient include generating stimulation with an electronic module and housing the electronic module in a housing. The housing has a shape allowing the housing and a surgical device to be accommodated together within an insertion tool used to insert the housing into the patient.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Implantable stimulators and methods for stimulating a stimulation site within a patient are described herein. An exemplary implantable stimulator includes an electronic module configured to generate stimulation and deliver the stimulation via one or more electrodes. The electronic module is housed in a housing that has a shape allowing the stimulator and a surgical device to be accommodated together within an insertion tool used to insert the stimulator into the patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment.

The appearance of the phrase "in one embodiment" in various places in the specification are not necessarily all referring to the same embodiment.

As used herein and in the appended claims, unless otherwise specifically denoted, the term "stimulation site" will be used to refer to any nerve, muscle, organ, or other tissue within a patient that is stimulated by an implantable stimulator. For example, in the case of urinary incontinence, the stimulation site may be, but is not limited to, any nerve or muscle in the pelvic floor. Nerves in the pelvic floor region that may be targeted for stimulation include, but are not limited to, the pudendal nerve, pelvic nerve, and the clitoral branches of the pudendal nerve.

Figure 1:
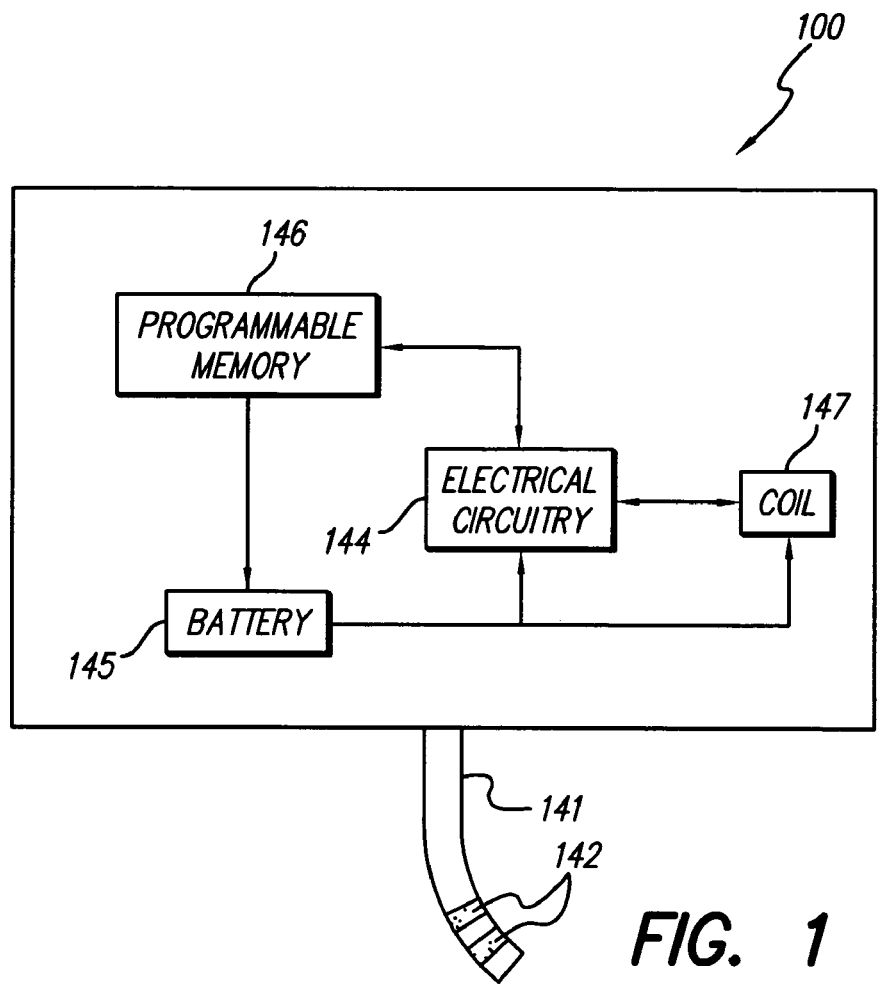
FIG. 1 is a block diagram illustrating a number of components of an exemplary implantable stimulator according to principles described herein.

FIG. 1 is a block diagram illustrating a number of components of an exemplary implantable stimulator (100). The stimulator (100) of FIG. 1 may be similar to a BION® microstimulator (Advanced Bionics® Corporation, Valencia, Calif.), for example. Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

It will be recognized that the stimulator (100) of FIG. 1 may alternatively include an implantable pulse generator (IPG) coupled to a lead of electrodes, a spinal cord stimulator (SCS), a cochlear implant, a deep brain stimulator, a drug pump, a micro-drug pump or any other type of implantable stimulator configured to deliver electrical and/or drug stimulation. Exemplary IPGs suitable for use as described herein include, but are not necessarily limited to, those disclosed in U.S. Pat. Nos. 6,381,496, 6,553,263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938,688; 6,016,449; and 6,539,263. Exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

As used herein and in the appended claims, unless otherwise specifically denoted, the terms "stimulator" and "microstimulator" will be used interchangeably to refer to any implantable stimulator that may be implanted within the patient and configured to provide electrical and/or other types of stimulation to a nerve, muscle, organ, and/or other tissue within a patient. The other types of stimulation may include, for example, drug stimulation wherein one or more stimulating drugs are infused into the nerve, muscle, organ, and/or other tissue.

As illustrated in FIG. 1, the stimulator (100) may include a number of components. It will be recognized that the stimulator (100) may include additional and/or different components as best serves a particular application. A battery (145) is configured to output voltage used to supply the various components within the stimulator (100) with power. The battery (145) may be a primary battery, a rechargeable battery, a capacitor, or any other suitable power source. A coil (147) is configured to receive and/or emit a magnetic field (also referred to as a radio frequency (RF) field) that is used to communicate with and/or receive power from one or more external devices (not shown) that are external to the body of the patient. Such communication and/or power transfer may include, but is not limited to, transcutaneously receiving data from the external device, transmitting data to the external device, receiving power from the external device to recharge the battery (145), and/or transmitting and receiving power and/or data to and/or from another implantable medical device. In some alternative embodiments, the stimulator (100) does not include an internal battery (145) and is instead powered transcutaneously and/or from other implantable medical devices via an RF field.

The stimulator (100) may also include electrical circuitry (144) configured to produce electrical stimulation pulses that are delivered to a nerve, muscle, and/or other tissue via one or more electrodes (142). The electrodes (142) may be located on a lead (141) that is coupled to the stimulator (100), as shown in FIG. 1. Alternatively, the electrodes (142) may be disposed in other locations as best serves a particular application.

In some embodiments, the stimulator (100) may be configured to produce monopolar electrical stimulation. The stimulator (100) may alternatively or additionally be configured to produce bipolar electrical stimulation. The electrical circuitry (144) may include one or more processors configured to decode stimulation parameters and generate the stimulation pulses. The electrical circuitry (144) may also include additional circuitry such as capacitors, integrated circuits, resistors, coils, and the like configured to perform a variety of functions as best serves a particular application.

The stimulator (100) may also include a programmable memory unit (146) for storing one or more sets of data and/or stimulation parameters. The stimulation parameters may include, but are not limited to, electrical stimulation parameters and drug stimulation parameters. The programmable memory (146) allows a patient, clinician, or other user of the stimulator (100) to adjust the stimulation parameters such that the electrical stimulation and/or drug stimulation are at levels that are safe and efficacious for a particular patient. The programmable memory (146) may be any type of memory unit including, but not limited to, random access memory (RAM), static RAM (SRAM), a hard drive, or the like.

Figure 2:
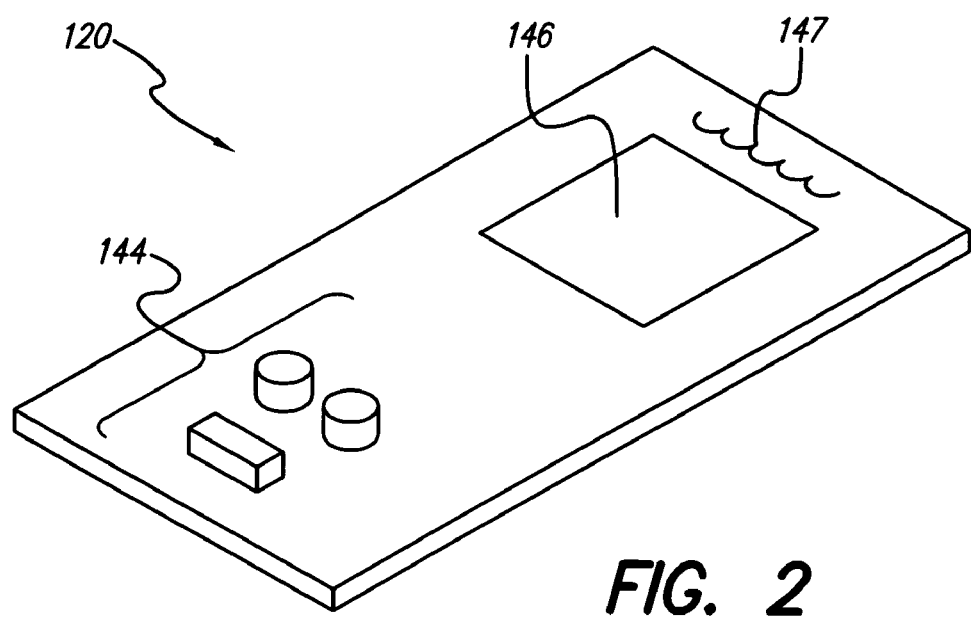
FIG. 2 shows that many of the components included in the stimulator may be organized into an electronic module according to principles described herein.

FIG. 2 shows that many of the components included in the stimulator (100; FIG. 1) may be organized into an electronic module (120). The electronic module (120) may include a printed circuit board (PCB), for example, that supports the programmable memory (146), the electrical circuitry (144), the coil (147), and any other component as best serves a particular application. The dimensions of the electronic module (120) may be configured such that the electronic module (120) may fit within a housing, as will be described in more detail below.

Figure 3:
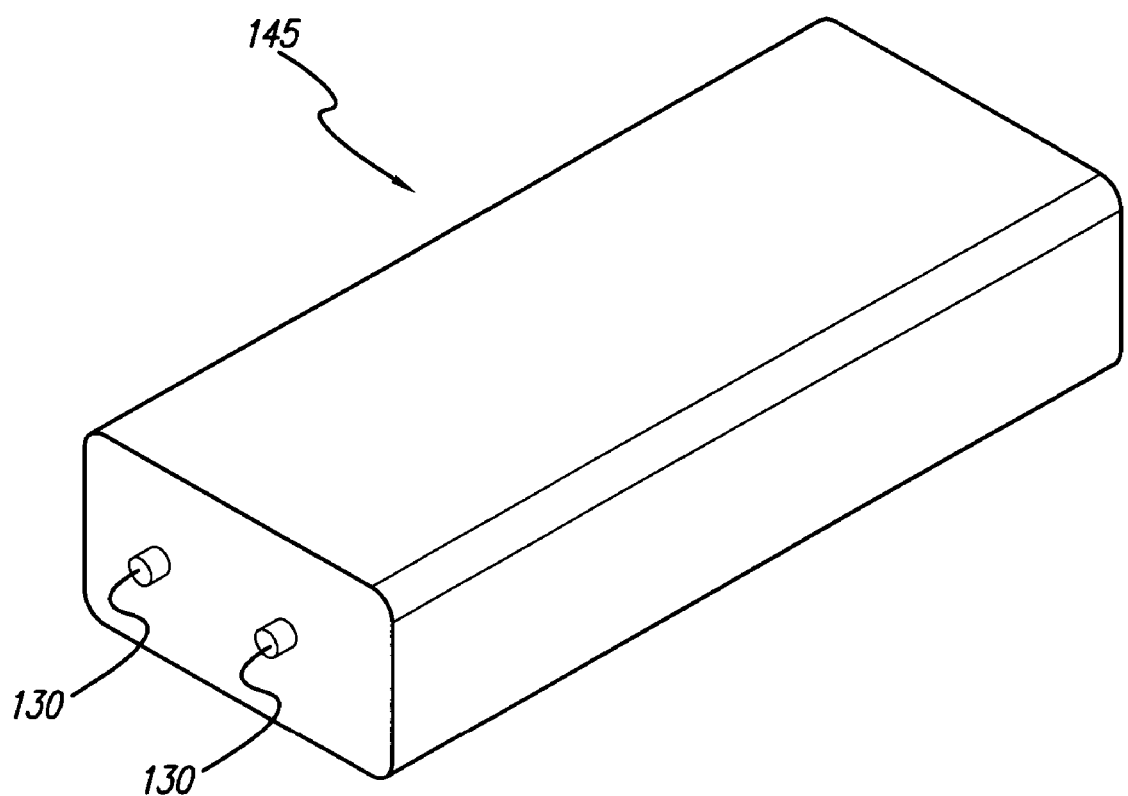
FIG. 3 shows an exemplary battery that may be used to supply the stimulator with power according to principles described herein.

FIG. 3 shows an exemplary battery (145) that may be used to supply the stimulator (100; FIG. 1) with power. The battery (145) may be any type of battery as best serves a particular application. The battery (145) includes terminals (130) that may be coupled to one or more of the components of the stimulator (100; FIG. 1). As shown in FIG. 3, the battery (145) may be in the shape of a long rectangular box. As will be shown in more detail below, the battery (145) may have a length approximately equal to the length of the electronic module (120; FIG. 2).

In some embodiments, the relatively large size of the battery (145) allows the stimulator (100; FIG. 1) to operate for up to five or more years, for example, without having to be replaced. It will be recognized that the operating life of the stimulator (100; FIG. 1) may be any amount of time. In some embodiments, the stimulator (100; FIG. 1) is explanted and replaced once the power in the battery (145) has been depleted. Because the implantation procedure is relatively simple and non-traumatic, many patients prefer to replace the entire stimulator (100; FIG. 1) every 5 years, for example, rather than recharge the battery (100; FIG. 1) on a regular (e.g., daily) basis. However, in some alternative embodiments, the battery (145) may be recharged on a periodic basis.

Figure 4:
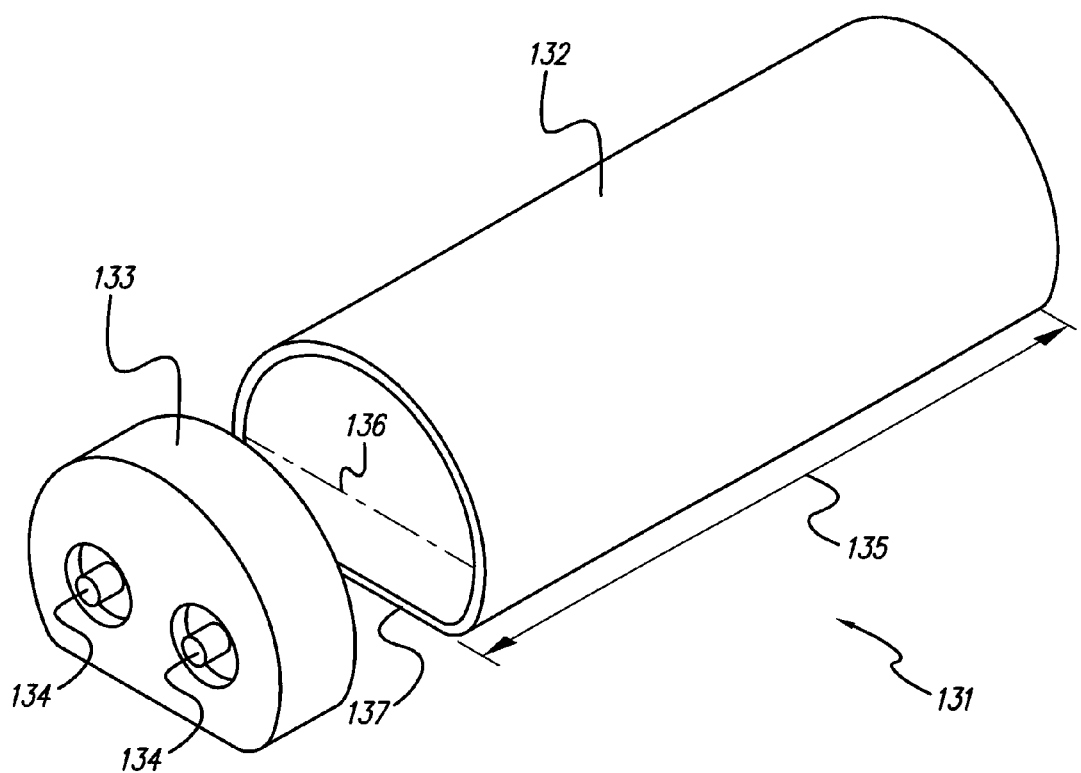
FIG. 4 illustrates an exemplary housing that may be used to house the electronic module and the battery according to principles described herein.

FIG. 4 illustrates an exemplary housing (131) that may be used to house the electronic module (120; FIG. 2) and the battery (145; FIG. 3) described above. As shown in FIG. 4, the housing (131) may include a main body (132) and a cap (133). The main body (132) has a length (135) and a diameter (136) which may be of any suitable dimension. For example, the length (135) may be approximately equal to 2 centimeters (cm) and the diameter (136) may be approximately equal to 12 millimeters (mm). However, it will be recognized that these dimensions are merely illustrative and that all of the dimensions of the housing (131) may be modified as best serves a particular application.

As shown in FIG. 4, the main body (132) has a partially cylindrical shape and includes a flat surface (137). As will be described in more detail below, the flat surface (137) is configured to allow a laparoscope or other surgical instrument along with the stimulator (100; FIG. 1) to be placed in a hollow cannula of an implantation tool that is used to implant the stimulator (100; FIG. 1). It will be noted that the main body (132) may have any shape as best serves a particular application. For example, the main body (132) may have multiple flat surfaces.

The cap (133) shown in FIG. 4 is configured to be placed over the open end of the main body (132) after the electronic module (120; FIG. 2) and the battery (145; FIG. 3) are entirely disposed within the main body (132) of the housing (131). The cap (133) may include a number of feed throughs (134) that may be used to electronically and/or physically couple a lead (141; FIG. 1) and/or other component to the stimulator (100; FIG. 1). The cap (133) may be laser welded to the main body (132) or otherwise coupled such that the housing is hermetically sealed after the electronic module (120; FIG. 2) and the battery (145; FIG. 3) are entirely disposed within the main body (132) of the housing (131).

The housing (131) may be made out of any suitable material. For example, the housing (131) may be made out of any metal such as titanium. Alternatively, the housing (131) may be made out of a semi-conductive or non-conductive material such as silicone, ceramic, or polyurethane.

Figure 5:
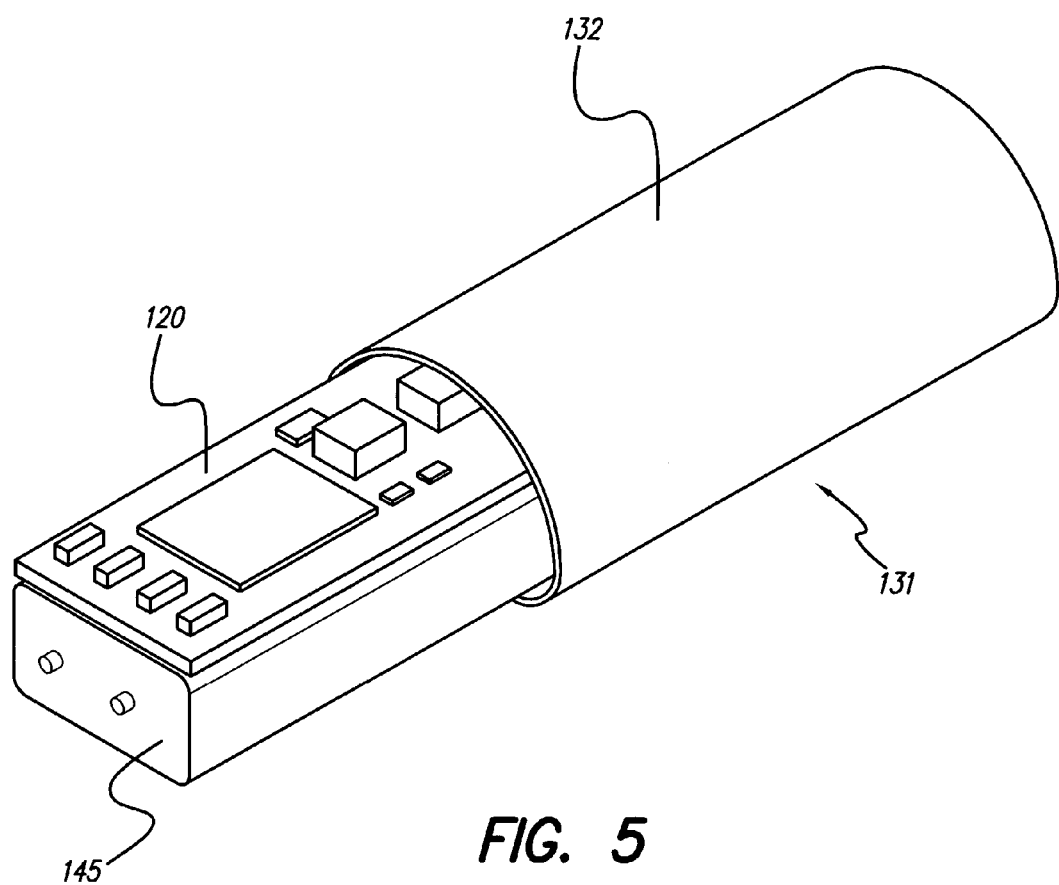
FIG. 5 shows the electronic module and the battery being inserted into the main body of the housing according to principles described herein.
Figure 6:
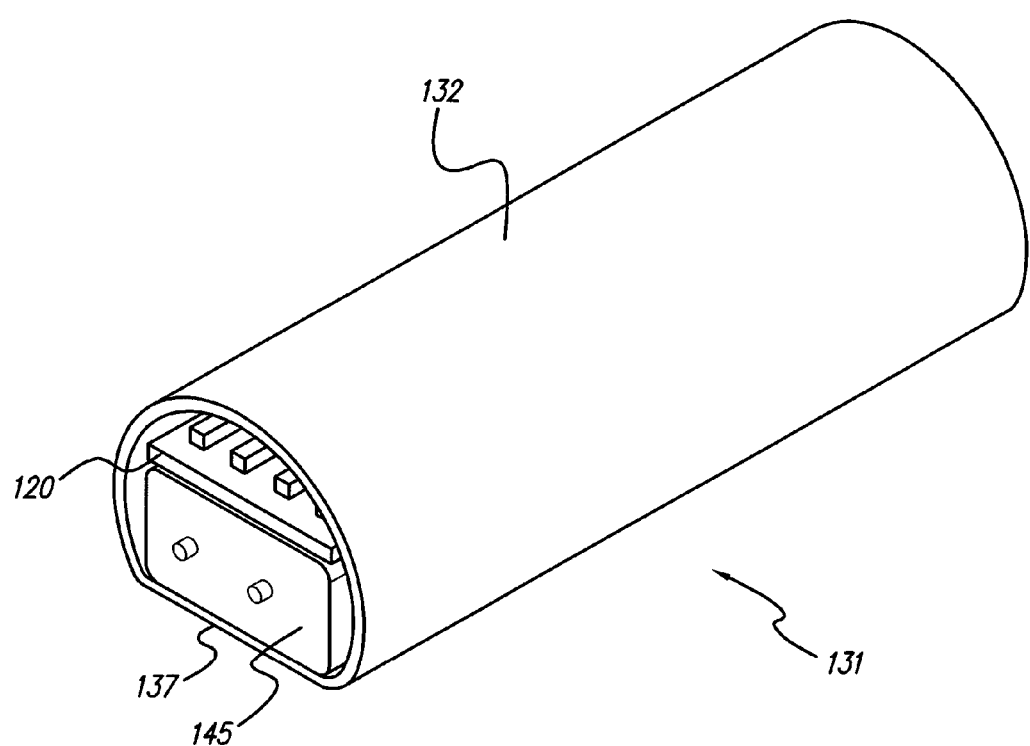
FIG. 6 shows the electronic module and the battery entirely disposed within the main body of the housing according to principles described herein.

FIG. 5 shows the electronic module (120) and the battery (145) being inserted into the main body (132) of the housing (131). As shown in FIG. 5, the electronic module (120) and the battery (145) are disposed within the main body (132) of the housing (131). In some embodiments, the inside portion of the main body (132) of the housing (131) includes guide structures (not shown) configured to guide the electronic module (120) and the battery (145) into position within the main body (132). FIG. 6 shows the electronic module (120) and the battery (145) entirely disposed within the main body (132) of the housing (131). Once the electronic module (120) and the battery (145) have been entirely disposed within the main body (132) of the housing (131), the cap (133; FIG. 4) maybe placed over the open end of the housing (131) as described in connection with FIG. 4.

Figure 7:
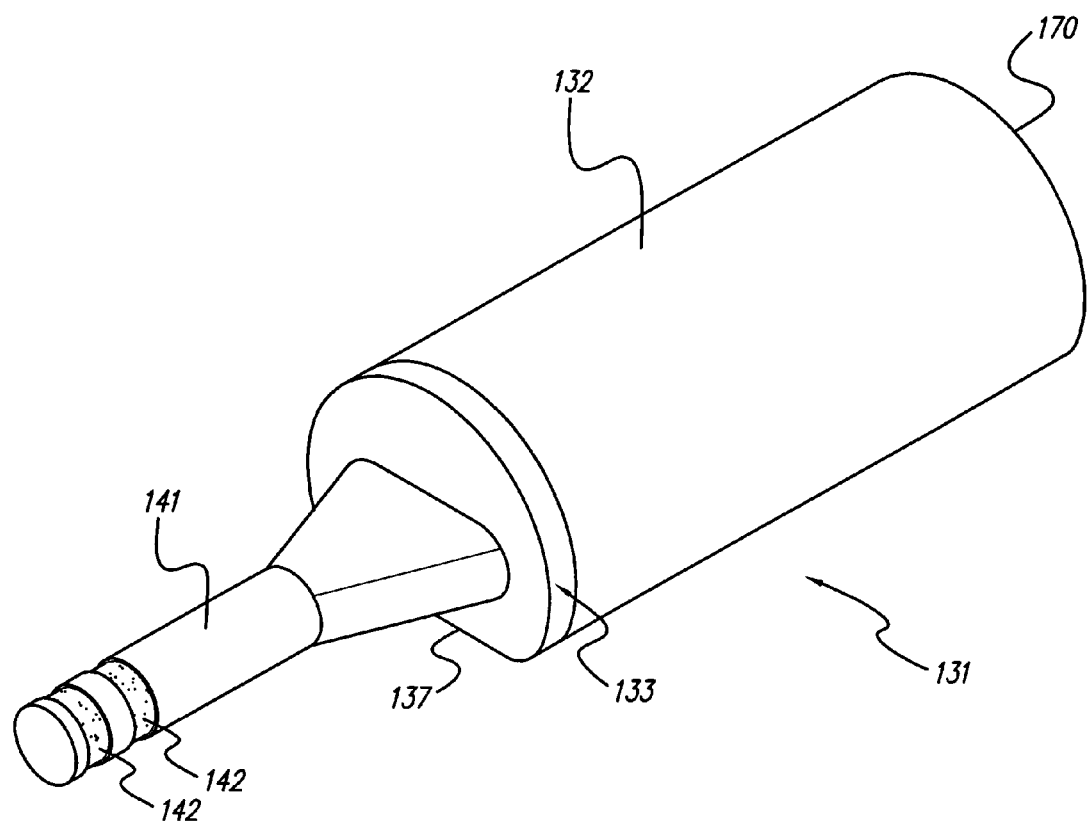
FIG. 7 shows a first perspective of a lead having a number of electrodes that is coupled to the housing according to principles described herein.
Figure 8:
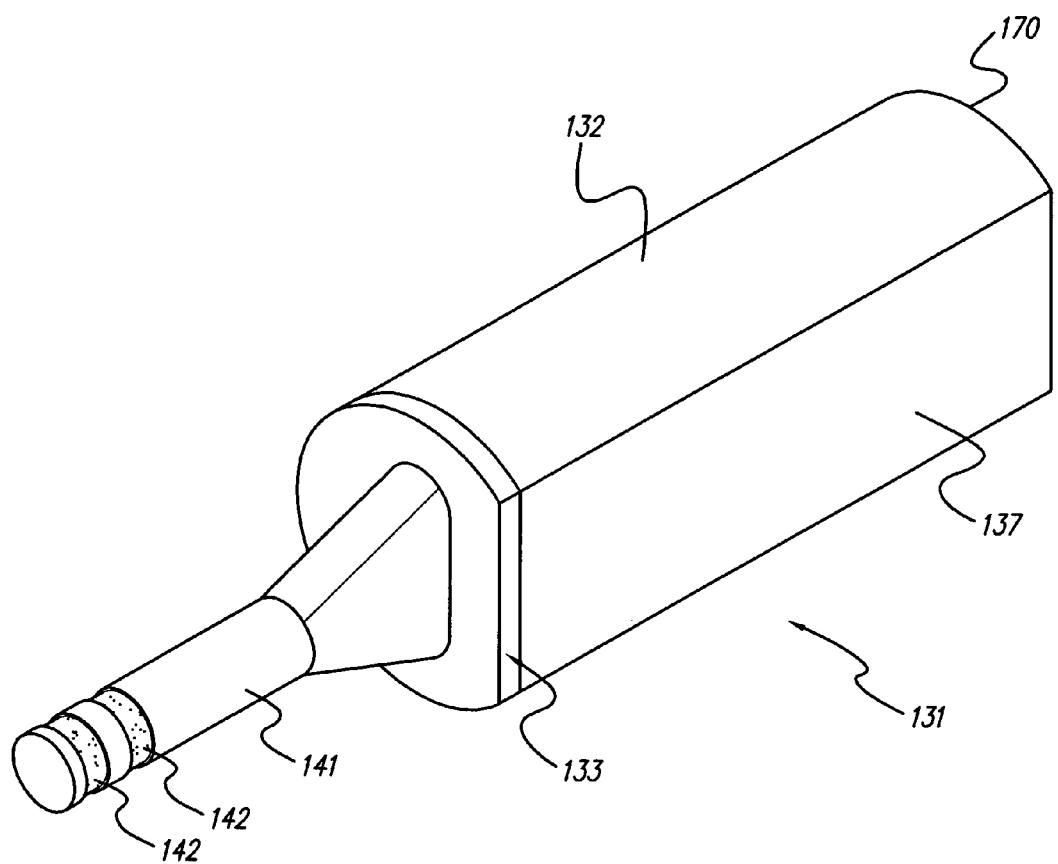
FIG. 8 shows a second perspective of a lead having a number of electrodes that is coupled to the housing according to principles described herein.

FIG. 7 shows a first perspective and FIG. 8 shows a second perspective of a lead (141) that is coupled to the housing (131). The lead (141) extends away from one of the ends of the housing (131) and supports a number of electrodes (142). For example, the lead (141) may be coupled to and extend away from the cap (133) that is hermetically sealed to the main body (132) of the housing (131), as shown in FIG. 7. The lead (141) may alternatively be coupled to an end (170) of the housing (131) opposite the cap (133). The lead (141) may be made out of a rigid material, such as metal or ceramic. Alternatively, the lead (141) may be a flexible wire or the like that may be guided to the stimulation site.

Figure 9:
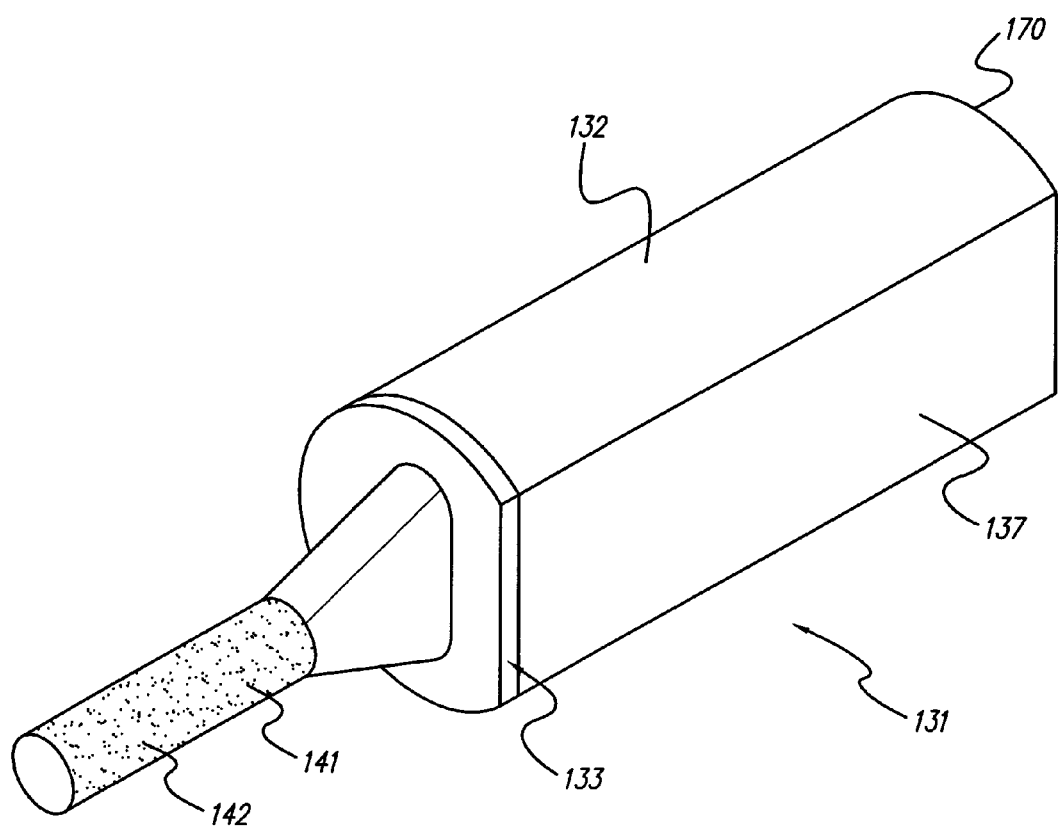
FIG. 9 shows a lead having a single electrode that extends across the entire length of the lead according to principles described herein.

There may be any number of electrodes (142) positioned along the lead (141). For example, there may be two electrodes (142) as shown in FIGS. 7 and 8. Moreover, the electrodes (142) maybe located at any position along the lead (141) and may have any size as best serves a particular application. For example, as shown in FIGS. 7 and 8, the electrodes (142) may be relatively small compared to the size of the lead (141) and may be located towards the distal end of the lead (141) as shown in FIGS. 7 and 8. Alternatively, as shown in FIG. 9, the lead (141) may include a single electrode (142) that extends across the entire length of the lead (141). A relatively large electrode such as the electrode (142) shown in FIG. 9 may be advantageous when it is desired to stimulate a relatively large stimulation site.

Figure 10:
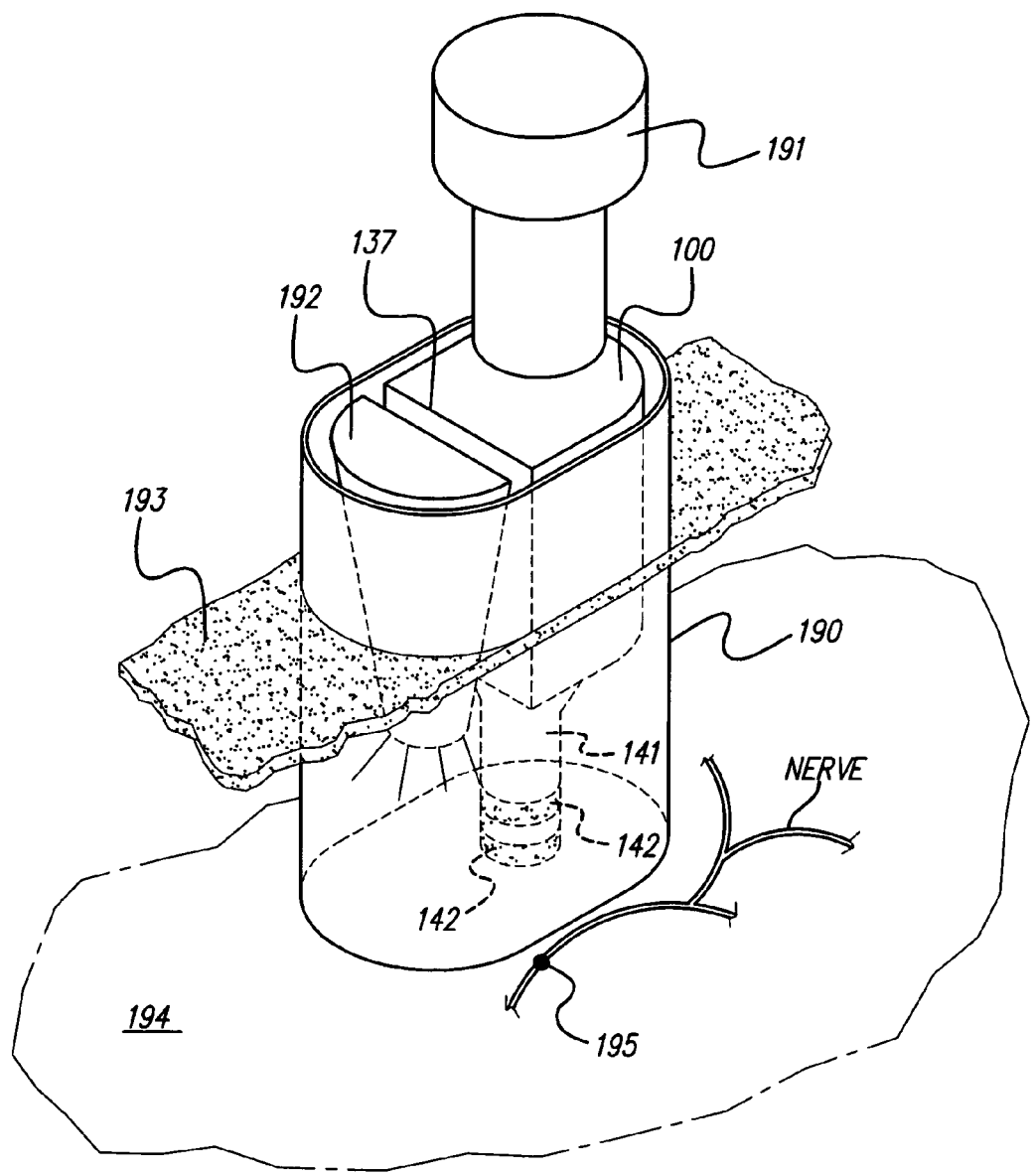
FIG. 10 illustrates that the stimulator may be implanted in a patient using a number of implantation tools according to principles described herein.

The stimulator (100; FIG. 1) may be implanted in a patient using a number of implantation tools (190, 191), as shown in FIG. 10. A hollow cannula (190) may be inserted through the skin (193) of the patient (194). The cannula (190) may be made from a stiff material with sufficient lubricity to permit the passage of the stimulator (100). As shown in FIG. 10, the stimulator (100) is inserted into the cannula (190). A push-rod (191) may be used to pass the stimulator (100) through the cannula (190) until the electrodes (142) are adequately placed at or near a stimulation site (195).

As shown in FIG. 10, a laparoscope (192) may also be inserted into the cannula (190) into the space adjacent to the flat surface (137) of the housing (131) of the stimulator (100). Additional or alternative surgical devices may be inserted into this space as best serves a particular application. The laparoscope (192) allows the physician inserting the stimulator (100) to visually locate the stimulation site (195), thereby ensuring accurate and optimal placement of the electrodes (142). Once the electrodes (142) have been optimally placed within the patient (194), the stimulator (100), lead (141), and/or electrodes (142) may be anchored in place using sutures and/or any other type of adhesive to prevent lead migration.

Hence, as shown in FIG. 10, the partially cylindrical shape of the housing (131) optimizes the limited space available within the cannula (190). If the cannula (190) has a shape other than a cylindrical shape, the shape of the housing (131) may be configured to match the shape of the cannula (190).

Figure 11:
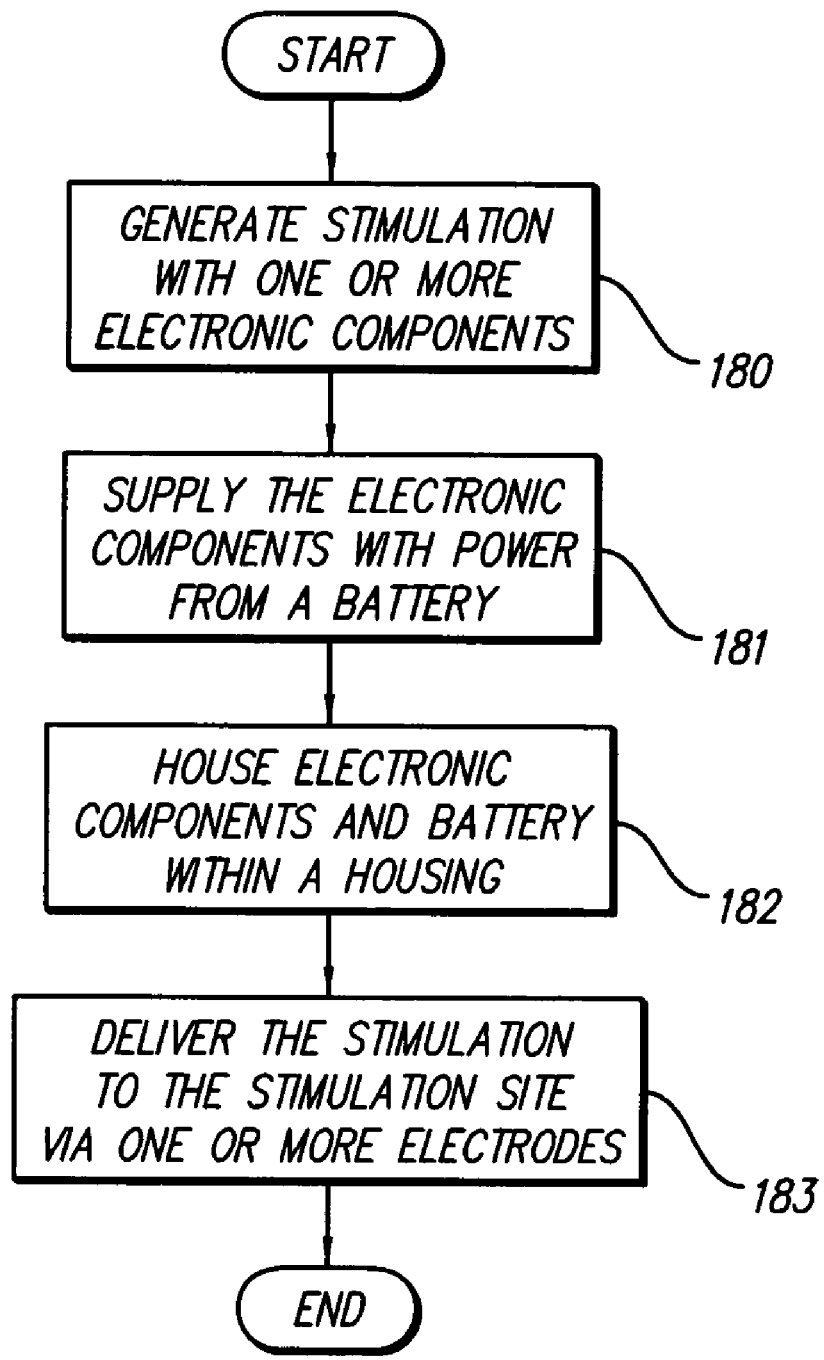
FIG. 11 is a flow chart illustrating an exemplary method stimulating a stimulation site within a patient according to principles described herein.

FIG. 11 is a flow chart illustrating an exemplary method of stimulating a stimulation site within a patient. The steps shown in FIG. 11 are merely illustrative and may be modified and/or added to as best serves a particular application. The stimulation is first generated with one or more electronic components (step 180). These electronic components may include the programmable memory (146; FIG. 2), the electrical circuitry (144; FIG. 2), the coil (147; FIG. 2), and any other component as best serves a particular application. These electronic components may be included in the electronic module (120; FIG. 2). The electronic components are supplied with power from a battery (145; FIG. 3) (step 181). The electronic module (120; FIG. 2) and the battery (145; FIG. 3)

are housed within a housing (131; FIG. 4) (step 182). The housing (131; FIG. 4) and a surgical device (e.g., a laparoscope (192; FIG. 9)) may then be jointly placed in a cannula (190; FIG. 9) of an insertion tool used to insert the housing (131; FIG. 4) into the patient. The stimulation is then delivered to the stimulation site via one or more electrodes (142; FIG. 7) (step 183).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A medical kit, comprising:
    an insertion tool including a lumen with a partially cylindrical surface extending therethrough;
    an elongated implantable stimulator comprising an electronic module configured to generate stimulation energy suitable for stimulating tissue and an elongated implantable housing enclosing the electronic module, the housing including a partially cylindrical longitudinal surface and a substantially flat longitudinal surface opposing the partially cylindrical longitudinal surface, and
    an elongated surgical tool including a substantially flat surface;
    wherein the implantable stimulator and the surgical tool are configured for being inserted into the lumen of the insertion tool together, such that the partially cylindrical surface of the stimulator is adjacent the partially cylindrical surface of the lumen, and the substantially flat surface of the implantable stimulator housing is adjacent the substantially flat surface of the surgical tool.

2. The medical kit of claim 1, further including a battery configured to supply the electronic module with power, wherein the housing encloses the battery.

3. The medical kit of claim 2, wherein the battery is rectangular.

4. The medical kit of claim 1, wherein the implantable stimulator further includes a lead coupled to the housing, the lead comprising one or more electrodes for delivering the stimulation energy.

5. The medical kit of claim 4, wherein the lead comprises a rigid structure coupled to and extending away from an end of the housing.

6. The medical kit of claim 1, wherein the partially cylindrical surface has an arc greater than 180 degrees.

7. The medical kit of claim 1, wherein the electronic module is hermetically sealed within the housing.

8. The medical kit of claim 1, wherein the electronic module comprises a printed circuit board to which electrical circuitry is mounted.

9. The medical kit of claim 1, wherein the stimulator is sized to be introduced into a patient via a minimally invasive procedure.

10. The medical kit of claim 1, wherein the housing includes a main body having an open cavity in which the electronic module is mounted, the housing further includes a cap mounted to the main body to seal the open cavity.

11. The medical kit of claim 10, wherein the cap includes an electronic feed through that connects one or more stimulation electrodes to the electronic module.

12. The medical kit of claim 11, further comprising a lead carrying the one or more stimulation electrodes.

13. The medical kit of claim 1, wherein the lumen of the insertion tool has another partially cylindrical surface extending therethrough, and the surgical tool includes a partially cylindrical longitudinal surface opposing the substantially flat longitudinal surface of the surgical tool, wherein the stimulator and the surgical tool are configured for being inserted into the lumen of the insertion tool together, such that the partially cylindrical surface of the stimulator is adjacent the other partially cylindrical surface of the lumen.

14. A method of using the medical kit of claim 1 within a patient, comprising:
    inserting the stimulator together with the surgical tool within the lumen of the insertion tool, such that the cylindrical surface of the stimulator is adjacent the cylindrical surface of the lumen, and the substantially flat surface of the implantable housing is adjacent the substantially flat surface of the surgical tool;
    introducing a distal end of the insertion tool within the patient; and
    deploying the stimulator from the lumen of the insertion tool to an implantation site within the patient.

15. The method of claim 14, wherein the insertion tool is a cannula.

16. The method of claim 14, wherein the surgical tool is a laparoscope, the method further operating the laparoscope to visualize the implantation site while the stimulator is deployed from the insertion tool.

17. The method of claim 14, further comprising anchoring the stimulator at the implantation site.

18. The method of claim 14, wherein the insertion tool has a push-rod, the method further comprising operating the push-rod to push to deploy the stimulator from the lumen of the insertion tool.

19. The method of claim 14, further comprising operating the stimulator to stimulate tissue adjacent the implantation site.

* * * * *